US007888105B2

(12) United States Patent
Saul et al.

(10) Patent No.: US 7,888,105 B2
(45) Date of Patent: Feb. 15, 2011

(54) ENZYMATIC PROCESS FOR STEREO-SELECTIVE PREPARATION OF CHEMICAL COMPOUNDS IN HYDROFLUOROCARBON SOLVENTS

(75) Inventors: Simon Joseph Philip Saul, Manchester (GB); Jason Micklefield, Cheshire (GB); Stuart Corr, Cheshire (GB)

(73) Assignee: Ineous Fluor Holdings Limited (GB)

( * ) Notice: Subject to any disclaimer, the term of this patent is extended or adjusted under 35 U.S.C. 154(b) by 783 days.

(21) Appl. No.: 10/549,357

(22) PCT Filed: Mar. 18, 2004

(86) PCT No.: PCT/GB2004/001180

§ 371 (c)(1), (2), (4) Date: Jan. 18, 2007

(87) PCT Pub. No.: WO2004/083444

PCT Pub. Date: Sep. 30, 2004

(65) Prior Publication Data

US 2007/0128705 A1 Jun. 7, 2007

(30) Foreign Application Priority Data

Mar. 19, 2003 (GB) ................................. 0306267.6

(51) Int. Cl.
*C12P 41/00* (2006.01)
(52) U.S. Cl. ...................................................... 435/280
(58) Field of Classification Search .................... None
See application file for complete search history.

(56) References Cited

U.S. PATENT DOCUMENTS

| 4,925,790 | A * | 5/1990 | Blanch et al. .................. 435/52 |
| 6,383,772 | B1 | 5/2002 | Nicola |
| 7,078,226 | B1 | 7/2006 | Ditrich et al. |

FOREIGN PATENT DOCUMENTS

| CA | 2 354 382 | 7/2000 |
| JP | 2001-515729 | 9/2001 |
| JP | 2002-526086 | 8/2002 |
| WO | WO 97/22712 A1 | 6/1997 |
| WO | WO 98/42687 A1 | 10/1998 |
| WO | WO 99/13098 A1 | 3/1999 |
| WO | WO 00/17384 A1 | 3/2000 |
| WO | WO 00/39324 A2 | 7/2000 |
| WO | WO 01/38292 A2 | 5/2001 |

OTHER PUBLICATIONS

Beier et al., "Eantiomeric partitioning using fluorous biphase methodology for lipase-mediated (tras)esterifications", Chem. Commun. 2002: 1680-1681.*
Janda et al., "Catalytic Antibodies with Lipase Activity and R or S Substrate Selectivity", Science 244 437-440 (1989).*
Smidt et al., "Preparation of Optically Pure Chiral Amines by Lipase-Catalyzed Enantioselective Hydrolysis of N-Acyl-Amines", Biotechnology Techniques 10 (5) : 335-338 (1996).*
Ferraboschi et al., "Lipase-catalyzed resolution of stereogenic centers in steroid side chains by transesterification in organic solvents: the case of a 26-hydroxycholesterol", Tetrandedron: Asymmetry 9 : 2193-2196 (1998).*
Nishio, T. et al, "Production of Optically Active Esters and Alcohols from Racemic Alcohols by Lipase-Catalyzed Stereoselective Transesterification in Non-Aqueous Reaction System," J. Biochem., vol. 105, No. 4, pp. 510-512, (1989).
Patel, R.M. et al, "Stereoselective Enzymatic Hydrolysis of 2-Cyclohexyl- and 2-Phenyl-1,3-Propanediol Diacetate in Biphasic Systems," Appl. Microbiol. Biotechnol., vol. 34, pp. 10-14, (1990).
Theil, F. et al, "Lipase-Catalyzed Transesterification of Meso-Cyclopentane Diols," Tetrahedron, vol. 47, No. 36, pp. 7569-7582, (1991).
Johnson, C.R. et al, "Enzymatic Asymmetrization of Meso-2-Cycloalken-1,4-Diols and Their Diacetates in Organic and Aqueous Media," Tetrahedron Letters, vol. 33, No. 48, pp. 7287-7290, (1992).
Theil, F. et al, "Kinetic Resolution of Acyclic 1,2-Diols Using a Sequential Lipase-Catalyzed Transesterification in Organic Solvents," J. Org. Chem., vol. 59, No. 2, pp. 388-393, (1994).
Carrea, G. et al, "Role of Solvents in the Control of Enzyme Selectivity in Organic Media," TibTech, vol. 13, pp. 63-70, Feb. 1995.
Broos, J. et al, "Activity and Enantioselectivity of Serine Proteases in Transesterification Reactions in Organic Media," J. Chem. Soc. Perkin Trans. 1, vol. 22, pp. 2899-2905, (1995).
Lemke, K. et al, "Lipase-Catalysed Kinetic Resolution of Phenylethan-1,2-Diol by Sequential Transesterification—the Influence of the Solvent," Tetrahedron: Asymmetry, vol. 7, No. 4, pp. 971-974, (1996).
Gill, J. et al, "Enantioselectivity of Lipase-Catalysed Transesterification of 2-Ethyl-1,3-Propanediol: Comparison of Lipases from Bacterial, Fungal and Animal Sources," Tetrahedron: Asymmetry, vol. 8, No. 13, pp. 2227-2230, (1997).
Kawashiro, K. et al, "Effect of Organic Solvents on Enantioselectivity of Protease Catalysis," Biotechnology and Bioengineering, vol. 53, No. 1, pp. 26-31, Jan. 5, 1997.
Lloyd, R.C. et al, "Probing the Specificity of the $S_1$', Leaving Group, Site of Subtilisin *Bacillus lentus* Using an Enzyme-Catalyzed Transesterification Reaction," Tetrahedron: Asymmetry, vol. 9, pp. 551-561, (1998).
Ghorpade, S.R. et al, "Desymmetrization of M*eso*-Cyclopenten-cis-1,4-Diol to 4-(R)-Hydroxycylopent-2-en-1-(S)-Acetate by Irreversible Transesterification Using Chirazyme®," Tetrahedron: Asymmetry, vol. 10, pp. 891-899, (1999).

(Continued)

*Primary Examiner*—Sandra Saucier
(74) *Attorney, Agent, or Firm*—Cook Alex Ltd.

(57) ABSTRACT

A process for preparing a second compound stereo-selectively is described. The process comprises reacting a substrate comprising at least one first compound with a reagent in the presence of a biological catalyst and a solvent comprising at least one (hydro)fluorocarbon so as to convert a first compound into the second compound.

7 Claims, 6 Drawing Sheets

OTHER PUBLICATIONS

Weber, H.K. et al, "'Watching' Lipase-Catalyzed Acylations Using $^1$H NMR: Competing Hydrolysis of Vinyl Acetate in Dry Organic Solvents," Tetrahedron: Asymmetry, vol. 10, pp. 2635-2638, (1999).

Carrea, G. et al, "Properties and Synthetic Applications of Enzymes in Organic Solvents," Angew. Chem. Int. Ed., vol. 39, pp. 2226-2254, (2000).

Klibanov, A.M., "Improving Enzymes by Using Them in Organic Solvents," Nature, vol. 409, pp. 241-246, Jan. 11, 2001.

Bornscheuer, U.T., "Methods to Increase Enantioselectivity of Lipases and Esterases," Current Opinion in Biotechnology, vol. 13, No. 6, pp. 543-547, (2002).

Cover Letter of Apr. 11, 2008 from Kyowa Patent and Law Office to which the Japanese Office Action with English translation dated Mar. 18, 2008 is attached from the Japanese application which corresponds to this application.

Corr, *1, 1, 1, 2-Tetrafluoroethane; from refrigerant and propellant to solvent*, pp. 55-67, Journal of Fluorine Chemistry 118 (2002).

\* cited by examiner

Figure 3
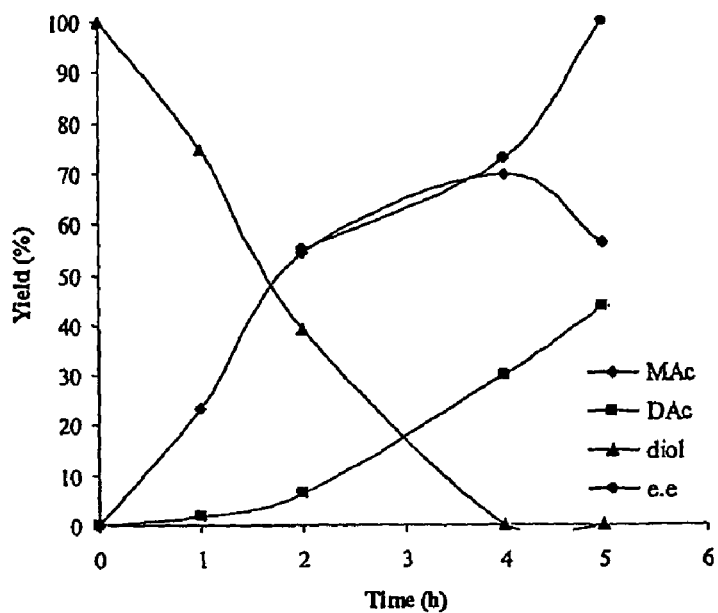
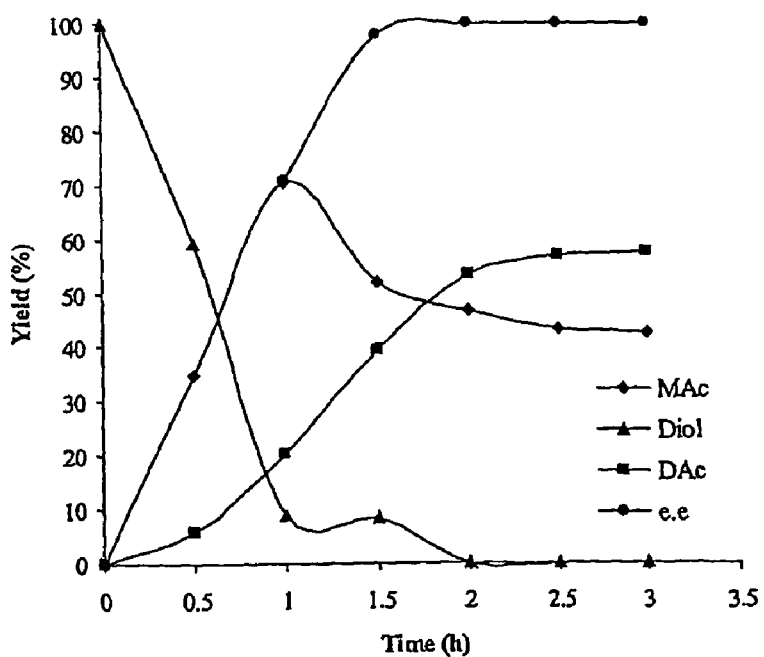
Figure 4

ENZYMATIC PROCESS FOR STEREO-SELECTIVE PREPARATION OF CHEMICAL COMPOUNDS IN HYDROFLUOROCARBON SOLVENTS

CROSS REFERENCE TO RELATED APPLICATIONS

This application is a national stage application based upon International Application No. PCT/GB2004/001180, filed Mar. 18, 2004, which claims priority from Great Britain Application No. GB 0306267.6, filed Mar. 19, 2003.

The present invention relates to a process for preparing a second compound by catalytic conversion of a first compound. More particularly, the invention relates to a process for stereo-selectively preparing a second compound by reacting a substrate comprising a first compound with a reagent in the presence of a biological catalyst.

Catalysts are materials that act to increase the rates of reactions without themselves being consumed by the reaction. Enzymes are natural catalysts that in many cases are sufficiently effective to reduce reaction activation energies to the point where the reaction becomes diffusion limited.

An outstanding feature of enzyme catalysis is the observed substrate specificity, which determines biological function. Some enzymes utilise only one biological substrate and are said to exhibit absolute substrate specificity. For example, glucokinase will catalyse the transfer of phosphate from ATP to glucose but to no other sugar. Other enzymes display much broader substrate specificity and are able to utilise structurally related molecules which are often dissimilar to their natural substrates. These enzymes are said to exhibit relative group specificity. An example of this kind of enzyme is *Candida cylindracea* (*C. cylindracea*) lipase, which will catalyse a transesterification reaction between a variety of acyl donors and acyl acceptors. In addition to chemical specificity, enzymes also exhibit stereochemical specificity.

The International Union of Biochemistry has classified enzymes into six categories according to the type of reaction that they catalyse.

Oxidoreductases catalyse oxidation and reduction reactions. More particularly, they catalyse the oxygenation of C—H, C—C and C=C bonds and the removal or addition of H atom equivalents.

Transferases catalyse the transfer of various groups such as aldehyde, ketone, acyl, sugar, phosphoryl or methyl groups.

Hydrolases catalyse the formation of, inter alia, esters, amides, lactones, lactams, epoxides, nitriles, anhydrides and glycosides by hydrolysis.

Lyases catalyse the addition-elimination of small molecules onto C=C, C=N and C=O bonds.

Isomerases catalyse isomerisation reactions such as racemisations and epimerisations.

Ligases catalyse the formation and cleavage of C—O, C—S, C—N and C—C bonds with concomitant triphosphate cleavage.

In nature, some enzymes function within or at the lipid layer within a cell membrane. The lipases, for example, are active at the water-lipid interface. The lipid layer provides a non-aqueous and non-polar environment for the working enzyme.

Enzyme catalysts are also used commercially in a number of processes in order to make use of their stereo-selectively. For example, enzymes of the hydrolase class (proteases and lipases) are used commercially for the resolution of racemic mixtures of secondary alcohols and carboxylic acids, in the conversion of prochiral and centrosymmetric compounds into chiral compounds and in the desymmetrisation of meso compounds. The enzymes operate most effectively in non-polar organic solvents, such as hexane. Increasing the polarity of the solvent tends to result in a rapid deactivation of the enzyme and/or a greatly reduced reaction rate.

It would be desirable to improve upon the commercial enzyme catalysed processes by improving the reaction rate, selectivity and/or conversion to products. It would also be desirable to employ a solvent which is able to dissolve a wide range of reaction substrates, which mitigates the deactivation of the enzyme during the reaction and which allows a given enzyme to be utilised effectively across a wide range of substrates.

In particular, there is a need for an enzyme catalysed process that can stereo-selectively convert a first compound into a second compound more efficiently than the known processes that are in commercial use today.

According to the present invention, there is provided a process for preparing a second compound stereo-selectively which process comprises reacting a starting material or substrate comprising at least one first compound with a reagent in the presence of a biological catalyst and a solvent comprising at least one (hydro)fluorocarbon.

The process of the present invention converts the at least one first compound, which may, for example, be an achiral compound, a racemic mixture of compounds, an enantiomerically pure substance, a meso compound, a prochiral compound or a centrosymmetric compound, into a particular chiral second compound or compounds stereo-selectively. By this we mean that the first compound(s), although capable, in principle, of reacting to form a mixture of stereoisomers, reacts preferentially or selectively under the influence of the biological catalyst to yield predominantly and preferably exclusively one enantiomer. In particular, we are referring to a process that yields one particular enantiomer predominantly and preferably exclusively. More particularly, the conversion of the starting material or substrate is such that the desired enantiomer is formed at an enantiomeric excess of greater than 50%, more preferably of greater than 70% and particularly of greater than 90%.

The process of the present invention can provide for good conversions of the first compound(s) to the second compound(s) at high stereo-selectivities. The conversions and stereo-selectivities may be better than are obtainable in the known commercial processes that use conventional hydrocarbon solvents such as hexane. Furthermore, the process may proceed at a faster rate than processes conducted in conventional hydrocarbon solvents.

It is also believed that the (hydro)fluorocarbon solvent that is used in the present process may result in less degradation of the biological catalyst than when the same reaction is conducted using conventional hydrocarbon solvents such as hexane. This, in turn, could allow a continuous process to be run for a longer period of time before changing the catalyst or in a batch process could allow the catalyst to be re-used a greater number of times.

The process of the present invention is conducted in the presence of a solvent that comprises at least one (hydro)fluorocarbon. By the term "(hydro)fluorocarbon" we mean a compound selected from the group consisting of the hydrofluorocarbons and the perfluorocarbons. By the term "hydrofluorocarbon" we mean a compound which contains only carbon, hydrogen and fluorine atoms. Hydrofluorocarbon solvents are preferred.

The solvent is usually in the liquid state, although we do not discount the use of supercritical fluids. Where the solvent comprises one or more low boiling compounds which are gases at room temperature, the desired liquid state may be attained by cooling the solvent to a suitably low temperature and/or by subjecting it to super-atmospheric pressures at some point in the process. One or both of these measures may be applied either before or after the (hydro)fluorocarbon solvent is mixed with the substrate to be reacted and, if necessary, continuously during the process.

Suitable (hydro)fluorocarbons may be selected from the $C_{1-10}$, particularly the $C_{1-5}$ and especially the $C_{1-4}$ (hydro)fluorocarbons.

Preferred perfluorocarbons include hexafluoroethane (R-116) and octafluoropropane (R-218).

Preferred hydrofluorocarbons are selected from the $C_{1-10}$, particularly the $C_{1-5}$ and especially the $C_{1-4}$ hydrofluoroalkanes. Suitable $C_{1-4}$ hydrofluoroalkanes include hydrofluoromethanes, such as trifluoromethane (R-23), fluoromethane (R-41) and difluoromethane (R-32); hydrofluoroethanes, such as pentafluoroethane (R-125), 1,1,1-trifluoroethane (R-143a), 1,1,2,2-tetrafluoroethane (R-134), 1,1,1,2-tetrafluoroethane (R-134a) and 1,1-difluoroethane (R-152a); hydrofluoropropanes, such as 1,1,1,3,3-pentafluoropropane (R-245fa), 1,1,2,2,3-pentafluoropropane (R-245ca), 1,1,1,2,3-pentafluoropropane (R-245eb), 1,1,2,3,3-pentafluoropropane (R-245ea), 1,1,1,2,3,3-hexafluoropropane (R-236ea), 1,1,1,2,2,3-hexafluoropropane (R-236cb), 1,1,1,3,3,3-hexafluoropropane (R-236fa), 1,1,1,2,3,3,3-heptafluoropropane (R-227ea) and 1,1,1,2,2,3,3-heptafluoropropane (R-227ca); and hydrofluorobutanes, such as 1,1,1,3,3-pentafluorobutane (R-356mfc). The preferred hydrofluorocarbons are R-32, R-134a, R-134, R-152a, R-143a, R-125, R-245fa, R-236ea and R-227ea, which are all low boiling making their removal from the reaction mixture at the end of the process relatively facile. Of these, R-32 and R-134a are particularly preferred, with R-134a being the most preferred.

Solvents containing mixtures of two or more (hydro)fluorocarbons may be used if desired.

The solvent which is used in the process of the present invention may also comprise an organic co-solvent in addition to the (hydro)fluorocarbon.

Suitable co-solvents include, inter alia, fluorine free and more particularly halogen free compounds. Suitable halogen free co-solvents will typically have a boiling point of 200° C. or below, for example in the range of from −85 to 200° C. The preferred co-solvents have a boiling point of 120° C. or below, for example in the range of from −85 to 120° C., more preferably 100° C. or below, for example in the range of from −70 to 100° C., and particularly 10° C. or below, for example in the range of from −60 to 10° C. Mixtures of two or more co-solvents may be used if desired.

Suitable co-solvents may be selected from the $C_{2-6}$, particularly the $C_{2-4}$ hydrocarbon compounds by which we mean compounds containing only carbon and hydrogen atoms. Suitable hydrocarbons include the alkanes and cycloalkanes, with alkanes such as ethane, n-propane, i-propane, n-butane, i-butane and n-pentane being preferred.

Other suitable co-solvents include the hydrocarbon ethers, by which we mean compounds having the formula $R^1$—O—$R^2$ in which $R^1$ and $R^2$ are independently hydrocarbyl groups containing only carbon and hydrogen atoms, such as $C_{1-6}$ and particularly $C_{1-3}$ alkyl groups. Suitable dialkyl ethers include dimethyl ether, methyl ethyl ether and diethyl ether.

Still further suitable co-solvents may be selected from the amides, sulphoxides, alcohols, ketones, carboxylic acids, carboxylic acid derivatives, inorganic acids and nitro compounds.

Suitable amide co-solvents include the N,N'-dialkylamides and alkylamides, e.g. dimethylformamide and formamide.

Suitable sulphoxide co-solvents include the dialkylsulphoxides, e.g. dimethylsulphoxide.

Suitable alcohol co-solvents include the aliphatic alcohols, particularly the alkanols. Suitable alkanols may be selected from the $C_{1-6}$, particularly the $C_{1-3}$ alkanols such as methanol, ethanol, 1-propanol and 2-propanol.

Suitable ketone co-solvents include the aliphatic ketones, particularly the dialkyl ketones such as acetone.

Suitable carboxylic acid co-solvents include formic acid and acetic acid.

Suitable carboxylic acid derivatives for use as co-solvents include the anhydrides, e.g. acetic anhydride, and the $C_{1-6}$, particularly the $C_{1-3}$ alkyl esters of $C_{1-6}$, particularly $C_{1-3}$ alkanoic acids, e.g. ethyl acetate.

Suitable nitro compounds for use as co-solvents include the nitroalkanes and nitroaryl compounds, e.g. nitromethane and nitrobenzene.

Although not preferred, when an organic co-solvent is used the solvent blend will typically comprise from 80.0 to 99.0% by weight of the (hydro)fluorocarbon and from 1 to 20% by weight of the co-solvent. Preferably, the solvent blend will comprise from 90.0 to 99.0% by weight of the (hydro)fluorocarbon and from 1 to 10.0% by weight of the co-solvent. As the polarity of the co-solvent is increased, it is generally desired to use less of the co-solvent in order to avoid any problems with deactivation of the enzyme.

As water is necessary for the proper functioning of most enzymes, the process of the present invention will typically be conducted in the presence of at least a small amount of water. However, the amount of water that is used will usually be such that the water does not form a separate phase in the reaction system. This is because an objective of the present process is to have the enzyme function in an environment that is predominantly composed of the (hydro)fluorocarbon solvent. Preferably, the amount of water is kept below the saturation level of the solvent that is used. More preferably, the reaction is conducted in the presence of less than 1% by weight of water based on the total weight of the solvent.

The process of the present invention is conducted in the presence of a biological catalyst. By a "biological catalyst", we mean a catalyst that can be found in biological tissues or systems. Particular biological catalysts for use in the process of the invention are the enzymes and abzymes. The biological catalyst must, of course, be capable of catalysing a stereoselective conversion of the substrate into the second compound.

Typically, the process of the present invention will be conducted in the presence of a single catalyst, although we do not discount the possibility that mixtures of catalysts may be used.

Suitable enzymes for use in the present process may be selected from any of the six classes of enzymes which have been identified supra.

The enzymes may be discrete in the sense that they have been isolated from the biological tissue in which they normally reside or else produced by over-expression in a host organism. These discrete enzymes may be used as they are or they may be lyophilised using standard literature processes, e.g. as described in Fitzpatrick, P. A., Klibanov, A. M., J. Am. Chem. Soc., 1991, 113, 3166. However, we have found that at least some enzymes are able to function as effectively in a (hydro)fluorocarbon solvent without prior lyophilisation, therefore offering the potential of avoiding a significant processing step.

The enzymes, whether lyophilised or not, are usually immobilised using standard literature processes. For example, the enzyme may be immobilised on a solid, insoluble matrix, for example by physical absorption or bonding. Suitable matrices include, inter alia, glass, diatomaceous earth, silica and organic polymers such as polystyrene and polyacrylate homopolymers and copolymers.

Alternatively, the enzymes may be part of a whole cell culture such as a live cell culture, e.g. *Lactobacillus acidophilus*, a resting cell culture, e.g. dried baker's yeast which can be activated by warm water or a non-viable cell culture which contains the enzyme and the required cofactor(s), e.g. dead yeast. The whole cell culture containing the enzyme will usually be immobilised on a solid, insoluble matrix, for example by physical absorption or bonding, using standard literature processes. The matrices discussed above may be used for this purpose.

Preferred enzymes for use in the process of the present invention include those in the hydrolase category. Particular enzymes are the proteases, such as *Subtilisin carlsberg* and *Subtilisin* BPN, the lipases, such as *Porcine pancreatic* lipase, *Candida antarctica* B lipase and *Pseudomonas cepacia* lipase and the glycosidases such as α- and β-galactosidase from *Aspergillus orgzea*.

Abzymes are catalytic antibodies, i.e. antibodies that are capable of catalysing specific chemical reactions. A suitable abzyme may be aldolase antibody 38C2.

The abzymes could be lyophilised and/or immobilised as discussed supra in connection with enzymes.

The process of the present invention is generally conducted at a temperature which provides for an acceptable rate of reaction and component solubility and which avoids significant degradation of the biological catalyst, the first compound(s) and the second compound(s). Typically, the process is conducted at a temperature in the range of from −60 to 120° C., preferably in the range of from −30 to 80° C. and particularly in the range of from 0 to 60° C., for example at about 20° C.

The process may be conducted at atmospheric, sub-atmospheric or super-atmospheric pressures. The precise operating pressure will depend, inter alia, on the solvent that is used, particularly its boiling point. Preferred operating pressures are in the range of from 0.1 to 200 bar, more preferably in the range of 0.5 to 30 bar and particularly in the range of from 1 to 15 bar.

The weight ratio of the (hydro)fluorocarbon solvent to the substrate to be reacted is preferably in the range of from 1:1 to 1000:1, more preferably in the range of from 1:1 to 500:1 and particularly in the range of from 1:1 to 10:1. The biological catalyst is typically used in very small amounts, for example of the order of $10^{-3}$ to $10^{-4}$ mole % of catalyst relative to the substrate. The precise amount will depend on the activity of the enzyme.

The process of the present invention can be usefully applied to various stereo-selective conversions. It is particularly useful for preparing compounds that can be used as intermediates in the manufacture of pharmaceutical compounds.

In one embodiment, the process of the present invention is used to resolve a racemic mixture or racemic modification by reacting that mixture with a reagent in the presence of the biological catalyst and (hydro)fluorocarbon solvent so as to preferentially or selectively react one of the enantiomers forming the mixture to form a new enantiomeric compound while leaving the other enantiomer largely or completely unreacted.

Accordingly, in one embodiment of the present invention there is provided a process of resolving a racemic mixture which process comprises reacting that mixture with a reagent in the presence of a biological catalyst and a solvent comprising at least one (hydro)fluorocarbon so as to preferentially or selectively convert one of the enantiomers forming the racemic mixture into a new enantiomeric compound.

The racemic mixture that is resolved in accordance with this embodiment of the present invention may be a racemic mixture of R and S alcohols, R and S carboxylic acids or esters, R and S amino acid esters, R and S amines, R and S thiols or R and S amides. Preferably, it is a mixture of R and S amino-acid esters. This particular resolution is effected by preferentially or selectively transforming a functional group attached to the chiral carbon(s) of either the R or S enantiomer. The biological catalyst is preferably an enzyme.

In a particular embodiment, the process is used to resolve the racemic N-P-dl-phenylalanine alkyl ester, where P denotes a protecting group, by a transesterification reaction in which the alkoxy group of either the R or S enantiomer is exchanged preferentially and preferably selectively by reaction with an alkanol that provides a different alkoxy group. Ordinarily, it is the S enantiomer that undergoes the transesterification reaction. The preferred protecting groups are acetyl and trifluoroacetyl and the preferred alkyl ester is propyl ester so that the preferred racemic mixtures are the N-acetyl-dl-phenylalanine propyl esters and the N-trifluoroacetyl-dl-phenylalanine propyl esters. The preferred alkanol is methanol. The biological catalyst is preferably an enzyme, more preferably a protease and even more preferably *Subtilisin carlsberg*.

The molar ratio of the N-P-dl-phenylalanine alkyl ester to the alkanol is preferably in the range of from 1:0.1 to 1:100, more preferably in the range of from 1:1 to 1:50 and particularly in the range of from 1:1 to 1:10.

The reaction time is typically in the range of from 0.1 to 48 hours, preferably in the range of from 1 to 36 hours and particularly in the range of from 1 to 24 hours.

The preferential/selective transesterification of the R or S enantiomer (normally the S enantiomer) of the racemic N-P-dl-phenylalanine alkyl ester is such that the desired enantiomer is typically formed at an enantiomeric excess of greater than 50%, preferably of greater than 70% and particularly of greater than 90%, e.g. 100%.

The resolution of the racemic N-acetyl-dl-phenylalanine propyl ester using methanol and assuming a 100% enantiomeric excess of the S enantiomer is shown in Equation (1).

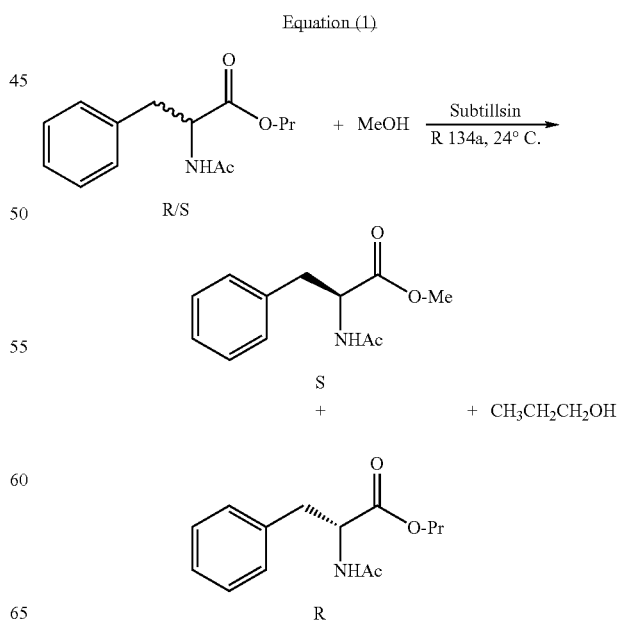

The resolution of N-trifluoroacetyl-dl-phenylalanine propyl ester using methanol (assuming once again that the S enantiomer is formed at a 100% enantiomeric excess) would proceed analogously.

In another embodiment, the process of the present invention is used to resolve racemic 1-phenylethanol, by a transesterification reaction in which the OH group of either the R or S enantiomer is exchanged preferentially and preferably selectively by reaction with a reagent. The reagent that is used is preferably an acyl donor, e.g. an enol ester, such as a vinyl or isopropenyl alkanoate, or an alkoxy enol ester. The preferred reagent is vinyl acetate. Ordinarily, it is the R enantiomer that undergoes the transesterification. The biological catalyst is preferably a lipase, for example *Candida antarctica* B Lipase.

The molar ratio of the 1-phenylethanol to the acyl donor is preferably in the range of from 1:0.1 to 1:100, more preferably in the range of from 1:1 to 1:50, for example 1:20.

The reaction time is typically in the range of from 0.1 to 48 hours, preferably in the range of from 1 to 36 hours and particularly in the range of from 1 to 24 hours.

The preferential/selective transesterification of the R or S enantiomer (normally the R enantiomer) of the racemic 1-phenylethanol is such that the desired enantiomer is typically formed at an enantiomeric excess of greater than 50%, preferably of greater than 70% and particularly of greater than 90%, e.g. 100%.

The resolution of the racemic 1-phenylethanol using vinyl acetate and assuming a 100% enantiomeric excess of the R enantiomer is shown in Equation (2).

Equation (2)

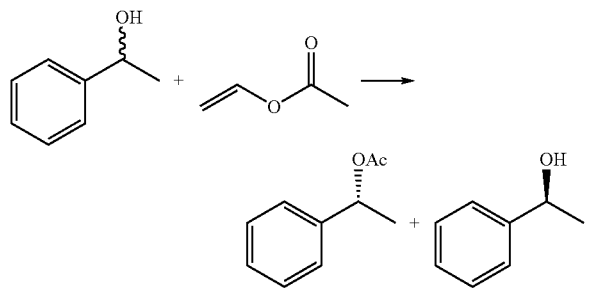

In another embodiment, the process of the present invention is used to prepare a particular enantiomer preferentially and preferably selectively from a meso compound by reacting the meso compound with a reagent in the presence of the biological catalyst and (hydro)fluorocarbon solvent. The reaction of the meso compound is also termed desymmetrisation, because the meso compound, which is symmetrical by virtue of it being superimposable on its mirror image, is converted into an enantiomeric product. An enantiomer, of course, cannot be superimposed on its mirror image.

Accordingly, in a further embodiment of the present invention there is provided a process of preparing a particular enantiomer preferentially or selectively from a meso compound which process comprises reacting the meso compound with a reagent in the presence of a biological catalyst and a solvent comprising at least one (hydro)fluorocarbon.

The process is effected by preferentially or selectively replacing or transforming a functional group attached to one of the chiral carbons.

The meso compound is preferably cis-4-cyclopentene-1,3-diol and the reagent that is used is preferably an acyl donor, e.g. an enol ester, such as a vinyl or isopropenyl alkanoate, or an alkoxy enol ester. The preferred reagent is vinyl acetate. However, other meso compounds and other reagents may be used.

The biological catalyst is preferably an enzyme and when the meso compound is cis-4-cyclopentene-1,3-diol, the enzyme is preferably a lipase and more preferably is *Porcine pancreatic* lipase, *Candida antarctica* B lipase or *Pseudomonas cepacia* lipase.

The reaction may be conducted in the presence of a hindered amine, particularly a tertiary amine such as triethylamine. The presence of the amine may contribute to faster reaction rates and greater conversions. However, omitting the enzyme can result in simpler downstream purification of the crude reaction mixture.

The reaction of meso cis-4-cyclopentene-1,3-diol with vinyl acetate proceeds as shown in Equation (3).

Equation (3)

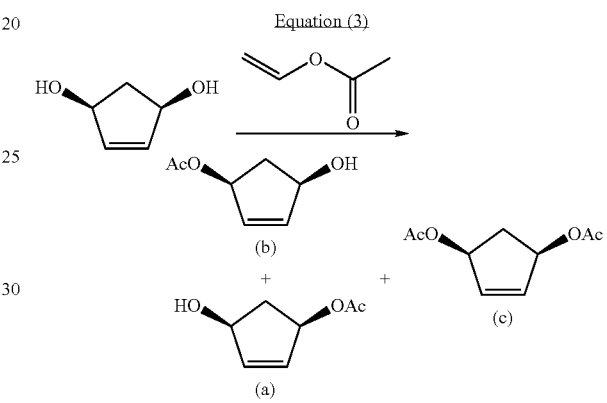

The process is believed to take place in two stages. The first stage is the stereo-selective formation of the enantiomeric mono-acetate product, i.e. (1R, 3S)-(+)-4-cyclopentene-1,3-diol-1-acetate (a), (1S, 3R)-(−)-4-cyclopentene-1,3-diol-1-acetate (b) or a mixture of enantiomers (a) and (b) with one of the enantiomers being in excess. When *Porcine pancreatic* lipase, *Candida antarctica* B lipase or *Pseudomonas cepacia* lipase is used as the enzyme the enantiomer (b) tends to be formed preferentially and often exclusively.

In the second stage, the mono-acetate (a) and/or (b) goes on to form the diacetate cis-4-cyclopentene-1,3-diacetate by reaction with a further molecule of the vinyl acetate. The diacetate, of course, is another meso compound.

Both of the monoacetate products are key starting materials in the synthesis of prostaglandins, prostacyclins and thromboxanes.

The molar ratio of the cis-4-cyclopentene-1,3-diol to the vinyl acetate is preferably in the range of from 1:0.1 to 1:100, more preferably in the range of from 1:1 to 1:50 and particularly in the range of from 1:1 to 1:20.

The reaction time is typically in the range of from 0.1 to 48 hours, preferably in the range of from 1 to 36 hours and particularly in the range of from 1 to 24 hours.

The reaction of the cis-4-cyclopentene-1,3-diol with the vinyl acetate normally proceeds so that the enantiomer that is formed preferentially/selectively (normally (1S, 3R)-(−)-4-cyclopentene-1,3-diol-1-acetate) is formed at an enantiomeric excess of greater than 50%, more preferably of greater than 70% and particularly of greater than 90%, e.g. 100%.

In yet another embodiment, the process of the present invention is used to prepare a particular enantiomer preferentially and preferably selectively from a prochiral compound by reacting the prochiral compound with a reagent in the presence of the biological catalyst and (hydro)fluorocarbon solvent. The reaction of the prochiral compound is also termed desymmetrisation, because an optically-inactive precursor is converted into a less-symmetrical, optically-active product.

Accordingly, in a further embodiment of the present invention there is provided a process of preparing a particular enantiomer preferentially or selectively from a prochiral compound which process comprises reacting the prochiral compound with a reagent in the presence of a biological catalyst and a solvent comprising at least one (hydro)fluorocarbon.

The process is effected by preferentially or selectively converting at least one achiral carbon atom into a chiral carbon atom with four different functional groups around the chiral centre.

The prochiral compound is preferably 2-ethylpropane-1,3-diol and the reagent that is used is preferably an acyl donor, e.g., an enol ester, such as a vinyl or isopropenyl alkanoate, or an alkoxy enol ester. The preferred reagent is vinyl acetate. However, other prochiral compounds and other reagents may be used.

The biological catalyst is preferably an enzyme and when the prochiral compound is 2-ethylpropane-1,3-diol, the enzyme is preferably a lipase and more preferably is *Pseudomonas cepacia* lipase.

The reaction of 2-ethylpropane-1,3-diol with vinyl acetate proceeds as shown in Equation (4).

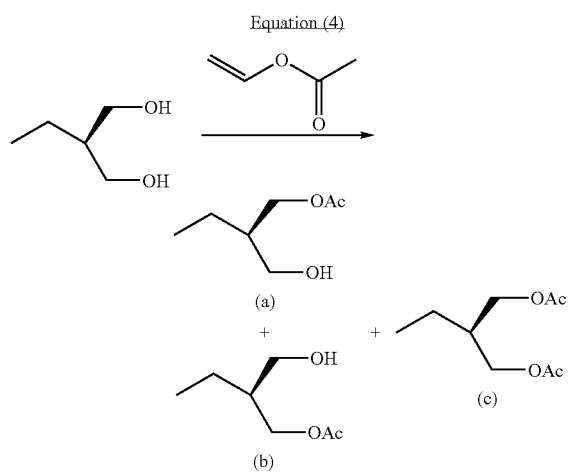

Equation (4)

As shown in equation (4), the pro-chiral 2-ethylpropane-1,3-diol is converted firstly to the monoacetate compound 1-hydroxy-3-acetoxy-2-ethylpropane. This conversion may result in the formation of the R or S enantiomer exclusively or may result in the formation of a mixture of the two enantiomers with one of the two predominating. When *Pseudomonas cepacia* lipase is used as the enzyme, the R enantiomer tends to be formed preferentially and often exclusively.

Thereafter, the monoacetate can go on to form the diacetate, 2-ethylpropane-1,3-diacetate, by reaction with a further molecule of the vinyl acetate. The diacetate, of course, is also prochiral.

Both of the mono-acetate products are key building blocks in the synthesis of platelet activating factor (as described in Faber, K., Biotransformations in Organic Chemistry, Springer-Verlag, 1997).

The molar ratio of the 2-ethylpropane-1,3-diol to the vinyl acetate is preferably in the range of from 1:0.1 to 1:100, more preferably in the range of from 1:1 to 1:50 and particularly in the range of from 1:1 to 1:10.

The reaction time is typically in the range of from 0.1 to 48 hours, preferably in the range of from 1 to 36 hours and particularly in the range of from 1 to 24 hours.

The reaction of the 2-ethylpropane-1,3-diol with the vinyl acetate normally proceeds so that the enantiomer that is formed preferentially/selectively (normally the R enantiomer) is formed at an enantiomeric excess of greater than 50%, more preferably of greater than 70% and particularly of greater than 90%, e.g. 100%.

The process of the present invention may be operated in batch mode or continuously. Where a (hydro)fluorocarbon solvent that has a boiling point below ambient is used, the reaction vessel will typically be a pressure vessel that is capable of withstanding elevated pressures.

In the batch process, the (hydro)fluorocarbon solvent is removed at the end of the process, e.g. by flash evaporation if the (hydro)fluorocarbon is a gas at ambient temperatures or by distillation, to yield a crude reaction mixture which can then be purified, if required, to isolate the desired second compound(s).

In a continuous process, a reactant stream comprising the (hydro)fluorocarbon solvent and the reactants is conveyed continuously through a reaction vessel containing the catalyst. Typically, the reactant stream is passed over a bed of immobilised catalyst. The crude reaction mixture that exits the reaction vessel is then treated, e.g. in a solvent evaporator, to remove the (hydro)fluorocarbon solvent and recover the one or more desired second compounds that have been formed in the process. The (hydro)fluorocarbon solvent that has been removed can be condensed and recycled if desired to minimise solvent infantries. Unreacted starting material may also be recycled if desired.

Where solvent is to be recycled, a suitable recovery system for low boiling point solvents, by which we mean solvents having a boiling point of 25° C. or below, e.g. 0° C. or below, comprises an evaporator into which the crude reaction mixture emerging from the process is passed, a compressor for compressing the vapour generated in the evaporator and a condenser for cooling the compressed vapour emerging from the compressor. The solvent is removed from the crude reaction mixture in the evaporator by flash evaporation induced by suction from the compressor and the solvent vapour so generated then passes to the compressor, which may be a diaphragm compressor, where it is compressed. From the compressor, the solvent vapour passes to the condenser where it is cooled and returned to liquid form for recharging to the process or possibly to a solvent reservoir supplying solvent to the process. The condenser, which may take the form of a coiled tube, can be arranged inside the evaporator so that the latent heat of condensation provides at least some of the energy required to evaporate the solvent.

A further suitable recovery system for low boiling point solvents comprises a solvent recycling circuit comprising an evaporator into which the reaction mixture emerging from the process is passed and in which the solvent is evaporated and a condenser in which the vapour emerging from the evaporator is cooled and returned to liquid form for recharging to the process or possibly to a solvent reservoir supplying solvent to the process. Heating of the evaporator and cooling of the condenser may be carried out independently, but in a preferred embodiment an external heat pump system is used to both heat the evaporator and to cool the condenser. The external heat pump system comprises an evaporator, a compressor, a condenser and an expansion valve which are sequentially arranged in a circuit through which a heat transfer fluid is caused to flow. The evaporator of the external heat pump system, which may take the form of a coiled tube, is arranged inside or around the outside of the condenser of the solvent recycling circuit so that evaporation of the heat transfer fluid in the evaporator cools the condenser and provides for the condensation of the solvent vapour passing through the solvent recycling circuit. The vapour generated in the evaporator of the external heat pump system is then compressed and passes to the condenser where it condenses and gives off heat. The condenser of the external heat pump system, which may also take the form of a coiled tube, is arranged inside or around the outside of the evaporator of the solvent recycling circuit so that the latent heat of condensation associated with the condensation of the heat transfer fluid provides the heat required to evaporate the solvent passing through the solvent recycling circuit. The condensed heat transfer fluid is then returned through an expansion valve to the evaporator so completing the cycle in the external heat pump system.

As an alternative to an external heat pump system, an external circulating heat-transfer fluid may be used to transfer the heat of solvent condensation to the evaporator vessel to provide heat for solvent evaporation.

When the process of the present invention is complete, the crude reaction mixture may be subjected to a purification step in order to isolate the desired product. The pure product may then be subjected to one or more further synthetic steps, e.g. to yield a pharmaceutical compound. Alternatively, the crude reaction mixture may be used directly in a further synthesis. Suitable purification techniques include those that are routinely used in chemical synthesis such as chromatography, crystallisation and distillation.

IN THE FIGURES

FIG. 3 is a time-course-plot for *Pseudomonas cepacia* catalysed desymmetrisation of cis-4-cyclopentene-1,3-diol in R-32 as studied in Example 7.

FIG. 4 is a time-course-plot for *Pseudomonas cepacia* catalysed desymmetrisation of cis-4-cyclopentene-1,3-diol in R-227ea as studied in Example 7.

Figure 1:
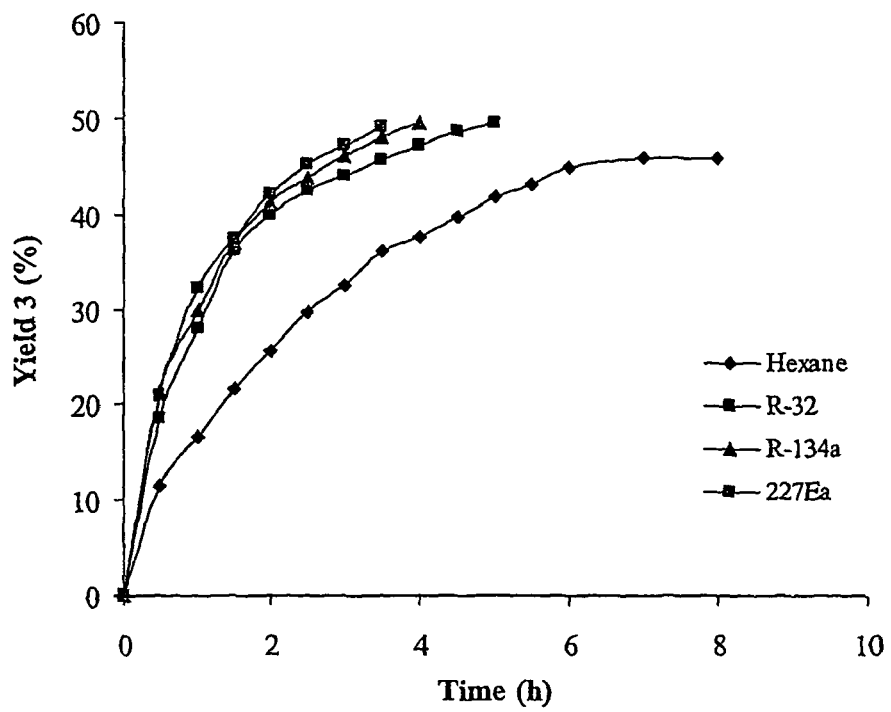
FIG. 1 is a time-course plot for the reactions studied in Example 6.
Figure 2:
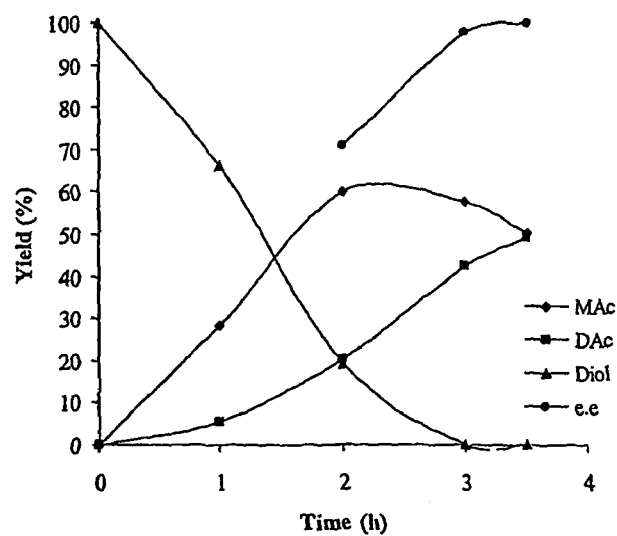
FIG. 2 is a time-course-plot for the *Pseudomonas cepacia* catalysed desymmetrisation of cis-4-cyclopentene-1,3-diol in R-134a as studied in Example 7.
Figure 5:
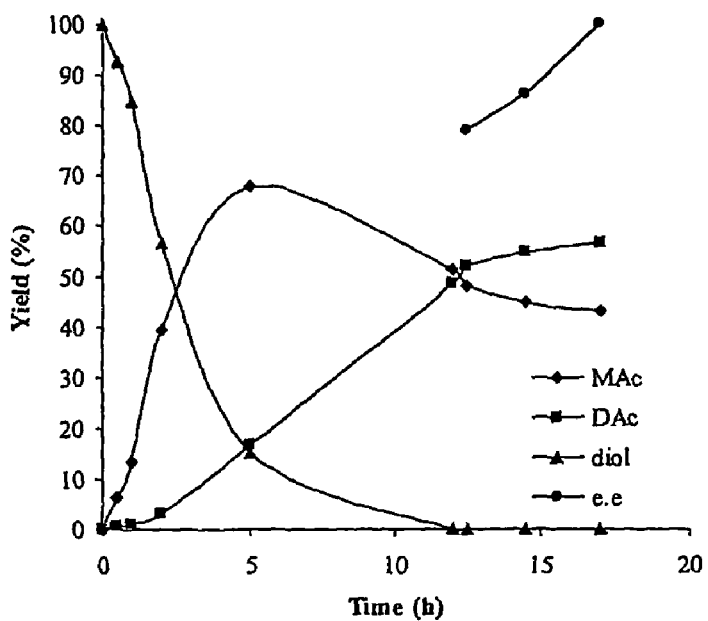
FIG. 5 is a time-course-plot for *Pseudomonas cepacia* catalysed desymmetrisation of cis-4-cyclopentene-1,3-diol in THF-$Et_3N$ as studied in Example 7.
Figure 6:
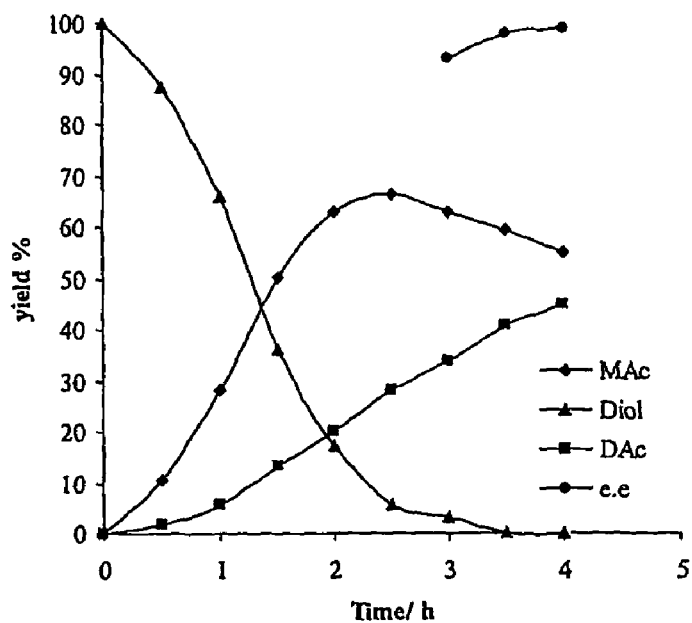
FIG. 6 is a time-course-plot for Novozym 435 catalysed desymmetrisation of cis-4-cyclopentene-1,3-diol in R-134a as studied in Example 7.
Figure 7:
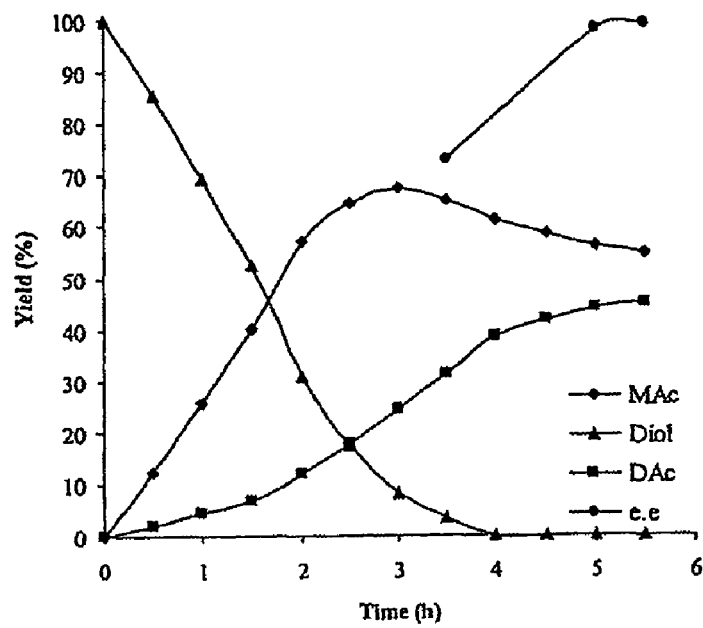
FIG. 7 is a time-course-plot for Novozym 435 catalysed desymmetrisation of cis-4-cyclopentene-1,3-diol in R-32 as studied in Example 7.
Figure 8:
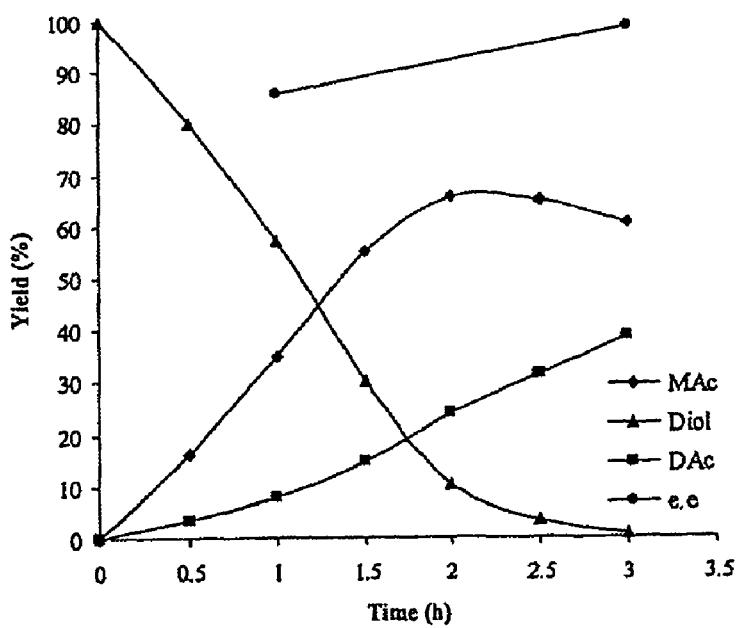
FIG. 8 is a time-course-plot for Novozym 435 catalysed desymmetrisation of cis-4-cyclopentene-1,3-diol in R-227ea as studied in Example 7.
Figure 9:
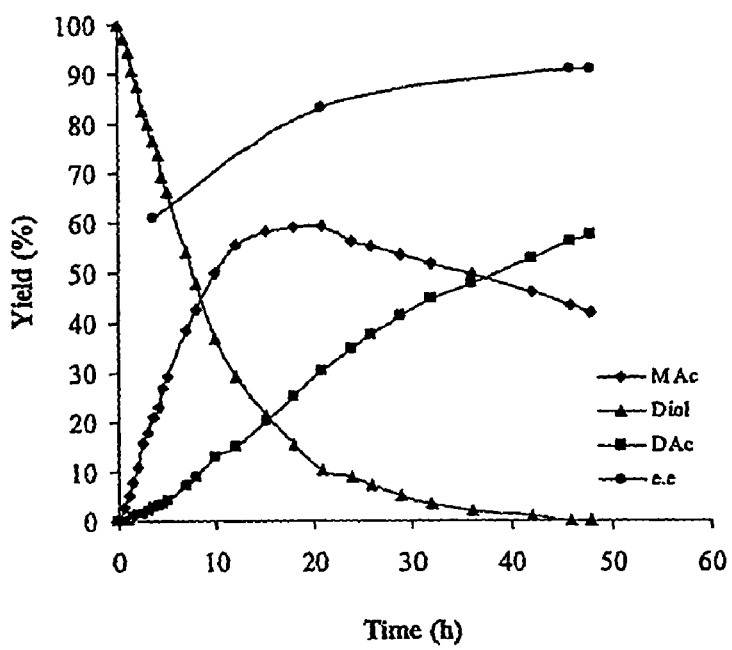
FIG. 9 is a time-course-plot for Novozym 435 catalysed desymmetrisation of cis-4-cyclopentene-1,3-diol in THF-$Et_3N$ as studied in Example 7.

The present invention is now illustrated but not limited by the following examples.

General Procedures

Preparation of N-trifluoroacetyl-dl-phenylalanine propyl ester

The racemic N-trifluoroacetyl-dl-phenylalanine propyl ester was prepared using the method disclosed by Curphey, T. J., J. Org. Chem., 1979, 44. 2805-2807 as follows:

To an oven dried flask was added phenyl alanine. The flask was then purged with $N_2$ gas and DMF (solvent), diisopropyl ethylamine (1 equivalent) and ethyl trifluoroacetate (1.25 equivalents)) were added. The solution was left to stir at 50° C. for seventeen hours, then, propyl iodide was added (1.25 equivalents). The solution was left to stir for a further 72 hours. The crude product was re-extracted and isolated by column chromatography using gradient elution. Starting with 400 ml hexane the polarity was gradually increased by adding 300 ml 9:1 hexane:ethyl acetate, then 300 ml 4:1 hexane:ethyl acetate, then 200 ml 3.5:1 hexane:ethyl acetate and finally 200 ml 2:1 hexane:ethyl acetate. The isolated yield was 4.17 g, 28%. The isolated product was then further purified by Kugelrohr distillation followed by recrystallisation from a mixture of petroleum spirit and ethyl acetate (9:1 respectively). The purified N-trifluoroacetyl-dl-phenylalanine propyl ester was a white crystalline solid. Product identity was confirmed by NMR and GC-mass spectroscopy.

Preparation of 2-ethylpropane-1,3-diol

The 2-ethylpropane-1,3-diol was prepared as follows:

To a solution of diethyl ethyl malonate (2.0 g, 10.7 mmol) was added a suspension of $LiAlH_4$ (2.5 equivalents) in dry ethanol at 0° C. The reaction mixture was allowed to warm to room temperature with stirring and after 1 hour was refluxed for a further 1 hour. After cooling in an ice bath, 1 ml of distilled water was added to the reaction mixture with stirring followed by 1 ml of 2M NaOH solution. The mixture was then filtered and the filtrate washed with ethyl acetate. The combined washings were evaporated under reduced pressure to leave a yellow oil which was purified by flash chromatography on silica using 5:1 ethyl acetate:hexane as the solvent. The product was obtained as an oil in 75% yield. Product identity was confirmed by NMR and GC-mass spectroscopy.

R-134a and R-32 were supplied by Ineos Fluor Ltd. and used without further purification. Both solvents were maintained in the liquid state under autogenous pressure by conducting the reaction in standard plastic-coated 10 ml glass aerosol bottles.

The enzymes were obtained from Aldrich Chemical Company, Sigma Chemical Company or Fluka Chemical Company and used without further treatment or after lyophilisation using the procedure described in Fitzpatrick, P. A., Klibanov, A. M., J. Am. Chem. Soc., 1991, 113, 3166.

The hydrofluorocarbons (R-134a, R-32 and R-227ea) were supplied by Ineos Fluor Limited. All other chemicals and solvents were purchased from Aldrich Chemical Company or Sigma Chemical Company and used without further purification.

Aerosols were supplied by Ineos Fluor Limited.

Gas chromatograms were recorded using a Shimadzu GC-17a instrument equipped with an HP SE-54 capillary column (25 m×0.21 mm i.d.). Chiral gas chromatograms were obtained on a Chrompack CP9001 instrument fitted with a Chiraldex GTA capillary column (30 m×0.25 mm i.d.).

Flame ionisation detectors were used in both cases and response factors calibrated for individual substances using standard solutions. The samples that were removed from the reacting mixture were taken up in dichloromethane solvent and where necessary naphthalene was used as an internal standard.

EXAMPLE 1

*Subtilisin carlsberg* catalysed resolution of racemic N-acetyl-dl-phenylalanine propyl ester In this Example, the resolution of the racemic N-acetyl-dl-phenylalanine propyl ester by converting the S enantiomer of the racemic mixture to the corresponding methyl ester using *Subtilisin carlsberg* was investigated. The reaction has been explained in greater detail supra.

A solution of 10 mM N-acetyl-dl-phenylalanine propyl ester and 200 mM methanol was prepared in each of the solvents hexane, tetrahydrofuran, and acetonitrile. To 4 ml of each solution was added 4.0 mg of lyophilised *Subtilisin carlsberg*. The resulting suspensions were stirred at room temperature and samples taken periodically for analysis by gas chromatography for both yield and enantiomeric excess.

The same reaction was also investigated using R-134a and R-32 as the solvents. Two mixtures of 10 mM N-acetyl-dl-phenylalanine propyl ester, 200 mM methanol and 4.0 mg of lyophilised *Subtilisin carlsberg* were prepared in glass aerosol bottles. The aerosol bottles were then capped, the caps crimped in place and a weighed quantity of the liquid hydrofluorocarbon solvent introduced through the aerosol valve from a larger pressure vessel. The resulting suspensions were then stirred magnetically at room temperature and samples of the reaction mixture were taken periodically for analysis by gas chromatography for both yield and enantiomeric excess. The samples were removed by venting a proportion of the reaction mixture through the valve into a sample vial. The hydrofluorocarbon solvent evaporated in the process to leave the low volatility residue of the reaction mixture in the sample vial. This residue was the taken up into a known quantity of solvent containing an internal standard, if required, for the GC analysis.

The reactants and products showed good solubility in each of the solvents examined. The results are presented in Table 1.

TABLE 1

| Solvent | Time (hours) | Conversion (%) | Enantiomeric Excess (% S enantiomer) |
|---|---|---|---|
| Hexane | 0.25 | 1.2 | — |
| | 0.5 | 3.5 | — |
| | 1 | 8.9 | 100 |
| | 2 | 17 | — |
| | 19 | 19.8 | 100 |
| Acetonitrile | 0.25 | 0.4 | — |
| | 0.5 | 0.8 | — |
| | 1 | 1.2 | — |
| | 2 | 1.4 | — |
| | 19 | 4.1 | 100 |
| Tetrahydrofuran | 0.25 | 0.8 | — |
| | 0.5 | 1.2 | — |
| | 1 | 1.6 | — |
| | 2 | 2.9 | — |
| | 19 | 7.9 | 100 |
| R-134a | 0.25 | 7.1 | — |
| | 0.5 | 11.2 | — |
| | 1 | 17.3 | — |
| | 2 | 22.2 | — |
| | 19 | 23.4 | 100 |

TABLE 1-continued

| Solvent | Time (hours) | Conversion (%) | Enantiomeric Excess (% S enantiomer) |
|---|---|---|---|
| R-32 | 0.25 | 0.51 | — |
| | 0.5 | 3.2 | — |
| | 1 | 8.3 | — |
| | 2 | 10.2 | — |
| | 19 | 13.4 | 100 |

It is clear from Table 1 that R-134a provides a more rapid reaction and greater ultimate conversion than the conventional solvents, such as hexane. Hexane is regarded generally as the best conventional solvent for the process of Example 1. R-32 shows good performance compared to each of acetonitrile and tetrahydrofuran and approaches hexane in the earlier parts of the reaction up to around 1 hour. Both R-134a and R-32 show excellent enantioselectivity.

EXAMPLE 2

*Subtilisin carlsberg* catalysed resolution of racemic N-trifluoroacetyl-dl-phenylalanine propyl ester Example 1 was repeated using 10 mM N-trifluoroacetyl-dl-phenylalanine propyl ester instead of N-acetyl-dl-phenylalanine propyl ester. This Example was conducted in order to test the sensitivity of the enzyme-solvent pair towards substrate specificity. The results are presented in Table 2.

TABLE 2

| Solvent | Time (hr) | Conversion (%) | Enantiomeric Excess (% S enantiomer) |
|---|---|---|---|
| Hexane | 0.25 | 1.6 | — |
| | 0.5 | 2.8 | — |
| | 1 | 4.2 | — |
| | 2 | 9.2 | — |
| | 19 | 21.1 | 100 |
| | 72 | 23.3 | 100 |
| Tetrahydrofuran | 0.25 | 0 | — |
| | 0.5 | 0 | — |
| | 1 | 0 | — |
| | 2 | 0.3 | — |
| | 19 | 0.63 | — |
| | 72 | 1.3 | — |
| R-134a | 0.25 | 3.7 | — |
| | 0.5 | 5.0 | — |
| | 1 | 5.8 | — |
| | 2 | 9.2 | — |
| | 19 | 22.1 | 100 |
| | 72 | 33.4 | 100 |
| R-32 | 1 | 5.9 | — |
| | 18 | 10 | 100 |

It is clear that with the use of the fluorinated N-protecting group, R-134a provides a distinct improvement in conversion compared to that obtained in hexane. In addition, when the solvent is R-134a, the process appears to continue at an appreciable rate beyond the 72 hours, whilst the rate observed for hexane is considerably lower. This may suggest that R-134a degrades the enzyme to a lesser degree than hexane. This property could allow the enzyme to be re-used to a greater degree in hydrofluorocarbon solvents than in the conventional organic solvents with consequent economic benefits.

The rate of reaction in tetrahydrofuran in this process is significantly reduced compared to Example 1. This shows that the hydrofluorocarbon solvents, in contrast to conventional solvents of similar polarity such as tetrahydrofuran, may allow the enzymes to function with greater efficacy across a wider range of substrates.

EXAMPLE 3

Lipase catalysed reaction of meso cis-4-cyclopentene-1,3-diol

In this Example, the enzyme catalysed reactions of cis-4-cyclopentene-1,3-diol with vinyl acetate in R-134a and tetrahydrofuran using *Porcine pancreatic* lipase were compared. This reaction has been explained in greater detail supra and results in the preferential formation of one particular enantiomer. The method followed was that described in Theil et al., Tetrahedron, 1991, 47, 7569.

The diol (1.0012 g, 1.0 mmol) and triethylamine (0.070 g, 0.7 mmol) were added to 0.5 g *Porcine Pancreatic* lipase (PPL) and vinyl acetate (0.600 g, 7 mmol). 2 ml of a solvent was immediately added and the reaction mixture stirred magnetically at room temperature for a defined time. The reaction using R-134a was conducted in a glass aerosol bottle using exactly the same technique as described in Example 1. Material was removed from the reaction mixture for GC analysis for both yield and enantiomeric excess and the results are presented in Table 3.

TABLE 3

| Solvent | Time (hours) | Yield a + b (%) | Yield c (%) | Enantiomeric excess (% b enantimer) |
| --- | --- | --- | --- | --- |
| Tetrahydrofuran | 2.5 | 49.2 | 40.3 | 88 |
| R-134a | 2.5 | 45.1 | 43.3 | 87 | a = (1R,3S)-(+)-4-cyclopentene-1,3-diol-1-acetate
b = (1S,3R)-(−)-4-cyclopentene-1,3-diol-1-acetate
c = cis-4-cyclopentene-1,3-diacetate Table 3 shows that, in the presence of triethylamine, R-134a is as efficient and selective a solvent as tetrahydrofuran in the desymmetrisation reaction using *Porcine Pancreatic* lipase. Tetrahydrofuran was found by Theil et al. to be the most effective of the conventional non-aqueous solvents.

EXAMPLE 4

Lipase catalysed reaction of meso cis-4-cyclopentene-1,3-diol

Example 3 was repeated using *Pseudomonas cepacia* lipase. R-32 was also investigated and this reaction, like the R-134a reaction, was conducted in a glass aerosol bottle. For the hydrofluorocarbon solvents, no triethylamine was added. The results obtained are shown in Table 4.

TABLE 4

| Solvent | Time (hours) | Yield a + b (%) | Yield c (%) | Enantiomeric excess (% b enantimer) |
| --- | --- | --- | --- | --- |
| Tetrahydrofuran | 0.5 | 21.5 | 24.1 | — |
|  | 2 | 68.4 | 23 | 9.4 |
|  | 19 | 49.5 | 50.5 | 100 |
| R-134a | 0.5 | 25.4 | 9.9 | — |
|  | 2 | 50.2 | 31.0 | 61 |
|  | 19 | 45.3 | 55.5 | 100 |

TABLE 4-continued

| Solvent | Time (hours) | Yield a + b (%) | Yield c (%) | Enantiomeric excess (% b enantimer) |
| --- | --- | --- | --- | --- |
| R-32 | 0.5 | 20.5 | 3.1 | — |
|  | 2 | 36.2 | 7.0 | 73 |
|  | 19 | 52.8 | 40.5 | 100 | a = (1R,3S)-(+)-4-cyclopentene-1,3-diol-1-acetate
b = (1S,3R)-(−)-4-cyclopentene-1,3-diol-1-acetate
c = cis-4-cyclopentene-1,3-diacetate From the results in Table 4, both R-134a and R-32 appear to show a higher degree of selectivity towards the generation of the chiral mono-ester (b) in the early stages of the reaction than tetrahydrofuran. This is shown by the considerably higher enantiomeric excess in the products by the 2 hour stage. In addition to this improved selectivity, R-134a and R-32 showed a high degree and rate of conversion in the absence of any added triethylamine, possibly providing a simpler downstream product isolation and purification procedure.

EXAMPLE 5

Lipase catalysed reaction of 2-ethylpropane-1,3-diol

In this Example, the enzyme catalysed reactions of 2-ethylpropane-1,3-diol with vinyl acetate in R-134a, R-32 and chloroform using *Pseudomonas cepacia* lipase were investigated. This reaction has been explained in greater detail supra and results in the preferential formation of one particular enantiomer.

The results that were obtained were compared to literature data obtained in chloroform (as disclosed in Gill et al., Tetrahedron, 1991, 47, 7569).

1.0 mmol of diol, 3.9 mmol of vinyl acetate and 0.01112 g of *Pseudomonas cepacia* lipase were mixed with 2 ml of a solvent and stirred magnetically at room temperature for 19 hours. The reactions using R-134a and R-32 were conducted in glass aerosol bottles using exactly the same technique as described in Example 1. The mixture was sampled and analysed by GC for both yield and enantiomeric excess and the results presented in Table 5.

TABLE 5

| Solvent | Time (hours) | Yield R and S enantiomers (%) | Enantiomeric excess (% R enantimer) |
| --- | --- | --- | --- |
| Chloroform | 19 | 70 | — |
| R-134a | 19 | 91 | 98 |
| R-32 | 19 | 46 | 32 |
| Chloroform* | — | 88 | 19 |

*Data obtained from Gill et al., Tetrahedron, 1991, 47, 7569.

As with the reactions of Examples 3 and 4, the transformations in R-134a and R-32 clearly show a significantly higher degree of enantioselectivity than that observed in the conventional solvent, chloroform.

EXAMPLE 6

Lipase catalysed resolution of racemic 1-phenylethanol

In this Example, the resolution of racemic 1-phenylethanol by converting the R enantiomer of the racemic to the corresponding acetate using *Candida antarctica* B Lipase was investigated. The process was carried out using various hydrofluorocarbon solvents and using hexane.

The reactions using a hydrofluorcarbon as the solvent were conducted as follows:

Novozym 435 (0.0095 g; 95 units-10,000 units/g (Immobilised *Candida antarctica* B Lipase)) was added to the 1-phenylethanol (0.0620 g; 0.5 mmol) and vinyl acetate (0.8609 g; 10 mmol) in an aerosol. The aerosol was sealed and charged with R-134a (6.0500 g; 5.00 ml), or R-32 (4.8000 g; 5.00 ml), or R-227ea (6.93000 g; 5.00 ml). The reaction was stirred magnetically at room temperature (about 20° C.). Samples were abstracted periodically by inversion of the aerosol and depression of the valve causing expulsion of a small volume (about 50 μl) of the reaction solution into a glass vial. The sample was then dissolved in dichloromethane (0.1 ml) and analysed by gas chromatography.

The reaction using hexane as the solvent were conducted as follows: Novozym 435 (0.0095 g; 95 units-10,000 units/g (Immobilised *Candida antarctica* B lipase)) was added to the 1-phenylethanol (0.0620 g; 0.5 mmol) and vinyl acetate (0.8609 g; 10 mmol) in a Suppelco™ vial. The hexane (5.00 ml) was then added. The reaction was stirred magnetically at room temperature (about 20° C.). Samples, 1 μl, were taken periodically using a Hamilton syringe (1 μl) and analysed by gas chromatography.

The results are presented in Table 6. The reaction time-courses in each solvent are presented graphically in FIG. 1.

TABLE 6

| Solvent | Time (hr) | Conversion (%)$^a$ | Enantiomeric Excess (S) (%)$^b$ | Enantiomeric Excess (R) (%)$^b$ |
| --- | --- | --- | --- | --- |
| R-134a | 4 | 49 | 96 | 99 |
| R-227Ea | 5.5 | 49 | 96 | 99 |
| R-32 | 5 | 50 | >99 | >99 |
| Hexane | 8 | 46 | 85 | 99 |

$^a$determined by GC;
$^b$determined by chiral GC

Until now, it has been widely accepted that transesterification reactions catalysed by lipases are most efficient in apolar-hydrophobic solvents such as hexane, (more polar solvents can strip the enzyme of its essential water) (G. Kirchner, M. P. Scollar, A. M. Klibanov *J. Am. Chem. Soc.* 1985, 107, 7072-7076 and A. Zaks, A. M. Klibanov *Proc. Natl. Acad. Sci. USA* 1985, 82, 3192-3196). The resolution of 1-phenylethanol in various hydrofluorocarbons was compared to the resolution of 1-phenylethanol under identical conditions in hexane. It is evident from the results in Table 6 that reaction is superior in all of the hydrofluorocarbons investigated, both in terms of yield and enantiomeric excess (e.e).

FIG. 1 is a time-course plot for the solvents studied in this Example. FIG. 1 clearly shows the superior activity of Novozym 435 in the hydrofluorocarbon solvents tested; the rates of reaction in the hydrofluorocarbon solvents are greater than in Hexane. Using R-32, a resolution yield of 50% of each enantiomer with enantiomeric excess of >99% for each (S-1 and R-3) was obtained. Similar results were obtained when the reaction was carried out in R-134a or R-227ea. However, when the reaction was carried out in hexane the yields and optical purities obtained were lower.

EXAMPLE 7

Lipase catalysed reaction of meso cis4-cyclopentene-1,3-diol using *Candida antarctica* B lipase or lipase from *Pseudomonas cepacia*

In this Example, the enzyme catalysed reactions of cis-4-cyclopentene-1,3-diol with vinyl acetate using *Candida antarctica* B lipase or lipase from *Pseudomonas cepacia* was investigated. The reactions were conducted in each of R-134a, R-32, R-227ea and THF-Et$_3$N.

The reactions using a hydrofluorcarbon as the solvent were conducted as follows:

Novozym 435 (0.0010 g; 10 units-10,000 units/g (Immobilised *Candida antarctica* B lipase)) or lipase from *Pseudomonas cepacia* (0.0050 g; 0.463 units-92.6 units/g powdered lyophilised enzyme)) was added to the cis-4-cyclopentene-1,3-diol (0.0050 g; 0.05 mmol)) and vinyl acetate (0.0869 g; 1 mmol)) in an aerosol. The aerosol was sealed and charged with R-134a (6.0500 g; 5.00 ml), or R-32 (4.8000 g; 5.00 ml), or R-227Ea (6.93000 g; 5.00 ml). The reaction was stirred magnetically at room temperature (about 20° C.). Samples were abstracted periodically by inversion of the aerosol and depression of the valve causing expulsion of a small volume (about 50 μl) of the reaction solution into a glass vial. The sample was then dissolved in dichloromethane (0.1 ml) and analysed by gas chromatography.

The reactions in anhydrous THF-Et$_3$N were conducted as follows:

Novozym 435 (0.0010 g; 10 units-10,000 units/g (Immobilised *Candida antarctica* B)) or lipase from *Pseudomonas cepacia* (0.0050 g; 0.463 units-92.6 units/g (powdered lyophilised enzyme)) was added to a solution (5.00 ml) of the cis-4-cyclopentene-1,3-diol (0.0050 g; 0.05 mmol)), vinyl acetate (0.0869 g; 1 mmol)) and triethylamine (0.0101 g; 0.1 mmol (Et$_3$N)) in anhydrous THF (5.00 ml) in a Suppelco™ vial. The reaction was stirred magnetically at room temperature (about 20° C.). Samples, 1 μl, were taken periodically using a Hamilton syringe (1 μl) and analysed by gas chromatography.

The results are presented in Table 7. The reaction time-courses in each solvent, for each enzyme, are presented graphically in FIGS. 2 to 11. In FIGS. 2 to 9, MAc stands for monoacetate, DAc stands for diacetate, diol states for cis-4-cyclopentene-1,3-diol and e.e. stands for enantiomeric excess.

TABLE 7

| Solvent | Time (hr) | Yield monoacetate (%)$^a$ | Enantiomeric Excess of monoacetate (%)$^b$ |
| --- | --- | --- | --- |
| *Pseudomonas Cepacia* | | | |
| R-134a | 3.5 | 53 | >99 |
| R-32 | 5 | 60 | >99 |
| R-227ea | 3 | 42 | >99 |
| THF-Et$_3$N | 17 | 43 | >99 |
| Novozym 435 | | | |
| R-134a | 4 | 55 | >99 |
| R-32 | 5.5 | 55 | >99 |
| R-227ea | 3 | 61 | >99 |
| THF-Et$_3$N | 48 | 42 | 91 |

$^a$determined by GC
$^b$determined by chiral GC

Until now, it has been widely accepted that the best solvent system for the reaction of cis-4-cyclopentene-1,3-diol and vinyl acetate catalysed by lipases is the THF-Et$_3$N system (F.

Theil, H. Schick, G. Winter, G. Reck *Tetrahedron* 1991, 47, 7569-7582, S. R. Ghorpade, R. K. Kharul, R. R. Joshi, U. R. Kalkote, T. Ravindranathan, *Tetrahedron Asymmetry* 1999, 10, 891-899 and C. R. Johnson, S. J. Bis *Tetrahedron Lett.* 1992, 33, 7287-7290). The desymmetrisation of cis-4-cyclopentene-1,3-diol in various hydrofluorocarbons was, therefore, compared with the same reaction carried out under identical conditions in THF-Et$_3$N. It is evident from the results provided in Table 7 that the reaction using *Pseudomonas cepacia* lipase when carried out in R-32 or R-134a is superior to the reaction carried out in THF-Et$_3$N (as evidenced by the greater yields of the monoacetate product). When the reaction is carried out in R-227ea the yield of the monoacetate product is roughly equivalent to that obtained when the reaction is carried out in THF-Et$_3$N, however, the yield is achieved in a much shorter time. When Novozym 435 lipase was used, superior yields of the monoacetate product were obtained in all of the hydrofluorocarbon solvents used, and shorter reaction times gave a greater enantiomeric excess compared with conducting the reaction in THF-Et$_3$N.

Figure 10:
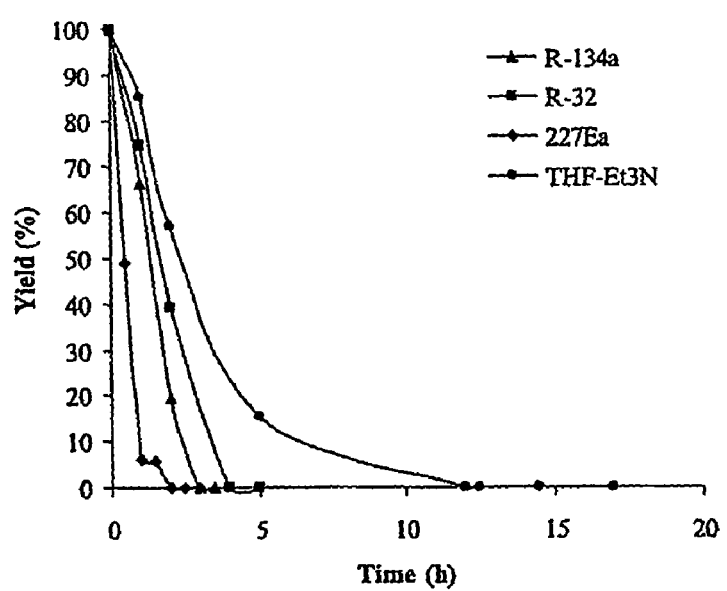
FIG. 10 is a time-course-plot for *Pseudomonas cepacia* catalysed desymmetrisation of cis-4-cyclopentene-1,3-diol in all four solvents used in Example 7, showing consumption of the diol.
Figure 11:
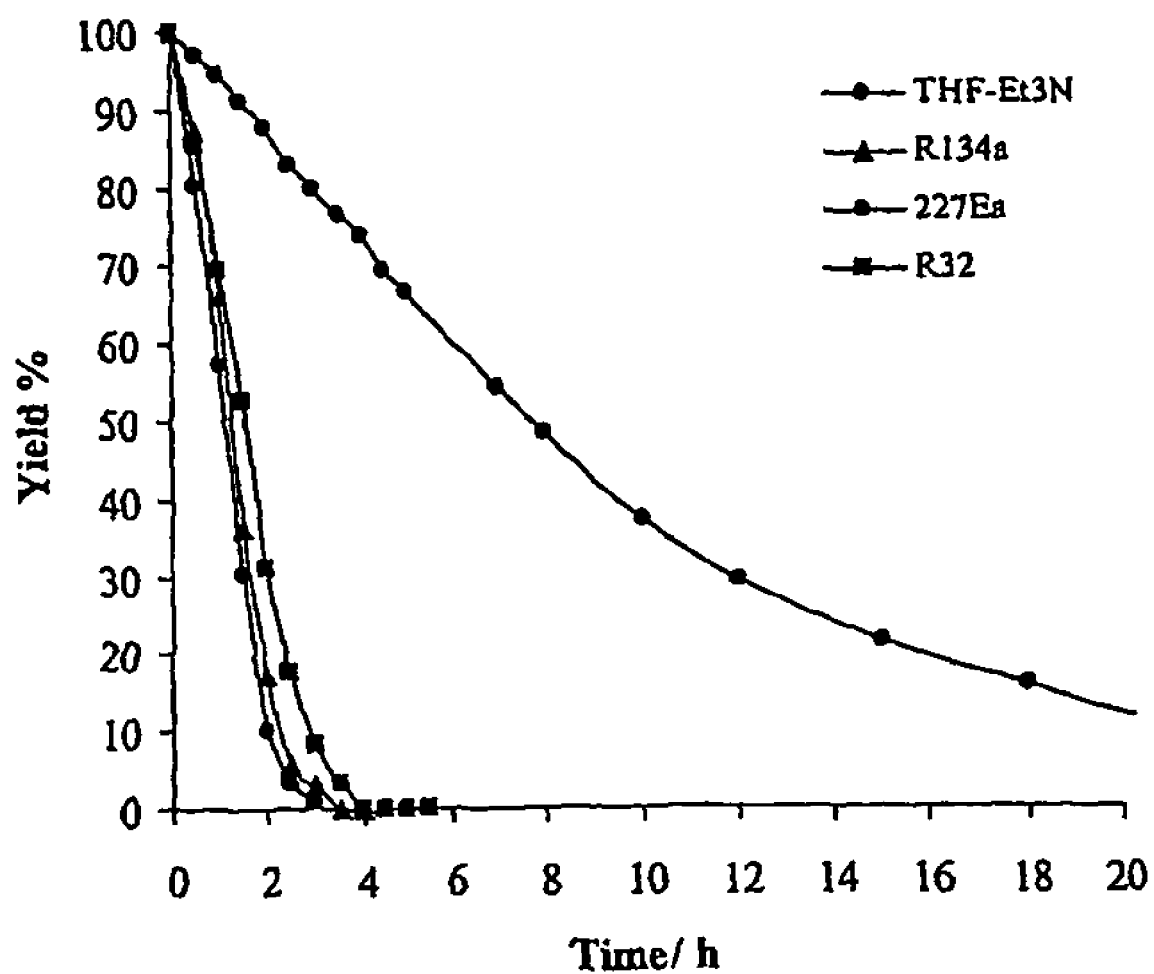
FIG. 11 is a time-course-plot for Novozym 435 catalysed desymmetrisation of cis-4-cyclopentene-1,3-diol in all four solvents used in Example 7, showing consumption of the diol.

This is also illustrated by FIGS. 2 to 11. For example, FIG. 10 shows the superior rates of reaction in the hydrofluorocarbon solvents, as illustrated by the steepness of the curves depicting the consumption of cis-4-cyclopentene-1,3-diol. Similar conclusions can be made from inspection of FIG. 11. It is clear that the rates of reaction in the hydrofluorcarbon solvents were found to be much greater than in THF-Et$_3$N. For the *Pseudomonas cepacia* lipase catalysed desymmetrisation of cis-4-cyclopentene-1,3-diol, the reaction in R-32 is the most efficient, delivering a 60% yield of the monoacetate product with 99% enantiomeric excess.

For Novozym 435 lipase catalysed desymmetrisation of cis-4-cyclopentene-1,3-diol, reaction in 227Ea was found to be the most efficient, giving a 61% yield of the monoacetate product with 99% enantiomeric excess.

The invention claimed is:

1. A process for preparing a second compound stereoselectively which process comprises reacting a substrate comprising at least one first compound with a reagent in the presence of a biological catalyst and a solvent comprising at least one (hydro) fluorocarbon, excluding trifluoromethane, which is conducted in the presence of water at a level which is less than that required for the water to form a separate aqueous phase in the reaction system.

2. A process as claimed in claim 1, wherein the biological catalyst is an enzyme.

3. A process as claimed in claim 2, wherein the enzyme is a hydrolase.

4. A process as claimed in claim 3, wherein the enzyme is selected from the proteases and lipases.

5. A process as claimed in claim 2, wherein the enzyme is part of a microbial whole cell culture.

6. A process as claimed in claim 1, wherein the biological catalyst is an abzyme.

7. A process as claimed in claim 1, wherein the substrate is reacted to form an enantiomer at an enantiomeric excess of greater than 50%.

* * * * *